(12) United States Patent
Allmendinger et al.

(10) Patent No.: US 9,992,854 B2
(45) Date of Patent: Jun. 5, 2018

(54) AUTOMATIC STIPULATION OF A SPECTRAL DISTRIBUTION OF X-RAY RADIATION OF A NUMBER OF X-RAY SOURCES

(71) Applicant: Siemens Aktiengesellschaft, Munich (DE)

(72) Inventors: Thomas Allmendinger, Forchheim (DE); Thomas Flohr, Uehlfeld (DE); Bernhard Schmidt, Fuerth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 373 days.

(21) Appl. No.: 14/430,583

(22) PCT Filed: Sep. 11, 2013

(86) PCT No.: PCT/EP2013/068816
§ 371 (c)(1),
(2) Date: Mar. 24, 2015

(87) PCT Pub. No.: WO2014/048748
PCT Pub. Date: Apr. 3, 2014

(65) Prior Publication Data
US 2015/0271903 A1     Sep. 24, 2015

(30) Foreign Application Priority Data

Sep. 27, 2012   (DE) .................. 10 2012 217 569

(51) Int. Cl.
*A61B 6/00*     (2006.01)
*H05G 1/32*     (2006.01)
(Continued)

(52) U.S. Cl.
CPC ............... *H05G 1/32* (2013.01); *A61B 6/032* (2013.01); *A61B 6/405* (2013.01); *A61B 6/4007* (2013.01);
(Continued)

(58) Field of Classification Search
CPC ....... A61B 6/032; A61B 6/4035; A61B 6/405; A61B 6/4241; A61B 6/4266;
(Continued)

(56) References Cited

U.S. PATENT DOCUMENTS 7,856,134 B2 *  12/2010  Ruhrnschopf ......... A61B 6/032
                                                 382/128
8,611,499 B2 *  12/2013  Spahn .................... A61B 6/08
                                                 378/63
(Continued)

FOREIGN PATENT DOCUMENTS

CN      101946299 A     1/2011
CN      102090900 A     6/2011

OTHER PUBLICATIONS

Chinese Office Action and English translation thereof dated Aug. 29, 2016.
(Continued)

*Primary Examiner* — Irakli Kiknadze
(74) *Attorney, Agent, or Firm* — Harness, Dickey & Pierce, P.L.C.

(57) ABSTRACT

An example embodiment relates to a method for automatically stipulating a spectral distribution of the X-ray radiation of a number of X-ray sources of a computed tomography system. This involves firstly stipulating start control parameters of an X-ray source, which determine the dose and spectral distribution of X-ray radiation. On the basis of an expected attenuation of the X-ray radiation by an examination object, an examination-object-specific basic control
(Continued)

parameter is then ascertained proceeding from the start control parameters. Afterwards, on the basis of the expected attenuation of the X-ray radiation by the examination object and the basic control parameter, first target control parameters and second target control parameters are ascertained for setting the spectral distribution of the X-ray radiation in a subsequent multi-energy measurement on the examination object. Moreover, a method, a control device suitable, and a computed tomography system comprising such a control device are described.

20 Claims, 3 Drawing Sheets

(51) Int. Cl.
*A61B 6/03* (2006.01)
*H05G 1/70* (2006.01)
(52) U.S. Cl.
CPC .............. *A61B 6/482* (2013.01); *A61B 6/544* (2013.01); *A61B 6/545* (2013.01); *H05G 1/70* (2013.01); *A61B 6/4014* (2013.01)
(58) Field of Classification Search
CPC ....... A61B 6/4411; A61B 6/482; A61B 6/484; A61B 5/1114; A61B 6/08; A61B 6/4441; A61B 6/4464; A61B 6/464; A61B 6/5235; A61B 6/542; A61B 6/545; A61B 6/589; A61B 6/504; G01T 1/2985; G06T 11/005; G06T 2211/408; G06T 11/006; G06T 11/003; G06T 7/0012; G06T 2207/10081; G06T 2211/412; G06T 2211/424; G06T 2211/432; G06T 2211/436; G06T 11/00; G06T 11/008; G06T 19/00; G06T 2200/04; G06T 2207/10116; G06T 2207/30008; H01L 2924/00014; H01L 2924/181; H01L 2224/73265; H01L 2924/00012; H01L 2224/8592; H01L 2224/48247; H01L 33/502; H01L 33/507; H01L 2224/73253; H01L 33/505; H01L 2224/13; H01L 2924/16195; C09K 11/7734
USPC .......................... 378/4, 5, 19, 62, 98.8, 98.9
See application file for complete search history.

(56) References Cited

U.S. PATENT DOCUMENTS

| 2008/0101535 A1* | 5/2008 | Wu ........................ A61B 6/032 378/19 |
| 2011/0007874 A1 | 1/2011 | Vogtmeier |
| 2011/0142312 A1 | 6/2011 | Toth et al. |
| 2011/0211669 A1* | 9/2011 | Herrmann ............... G01T 1/249 378/19 |

OTHER PUBLICATIONS

Yu L. et al; "Automatic selection of tube potential for radiation dose reduction in CT: A general strategy"; in: Med. Phys. 37 (1); 2010; pp. 234-243; ISSN: 0094-2405; 2010.
H. Alkadi et. al;; "State of the art low-dose CT angiography of the body"; Elsevier Ireland Ltd.; pp. 36-40; DOI: 10.1016/j.ejrad.2010.12.099; 2011; Dec. 29, 2010.
Kalender, Willi A. et al.: "Application- and patient size-dependent optimization of x-ray spectra for CT", in: Medical Physics ; vol. 36, No. 3; pp. 993-1007. (53 refs.), CODEN: MPHYA6 ISSN 0094-2405; DOI: 10.1118/1.3075901; XP012129929; 2009.
Murazaki et al; "Optimal Setting of Automatic Exposure Control Based on Image Noise and Contrast on Iodine-enhanced CT"; Academic Radiology; vol. 19; No. 4; pp. 478-484; ISSN: 1076-6332; DOI: 10.1016/j.acra.2011.11.011; XP055104742; 2012; Apr. 1, 2012.
International Search Report dated Mar. 11, 2014.
German Office Action dated Jun. 19, 2013.
Y. Lifeng, "Automatic selection of tube potential for radiation dose reduction in CT: A general strategy", Medical Physics, AIP, Melville, NY, US, vol. 37. Nr. 1. Dec. 10, 2009 (Dec. 10, 2009), 10 pages.
K. Willi, "Application- and patient size-dependent optimization of x-ray spectra for CT", Medical Physics, AIP, Melville, NY, US, vol. 36, No. 3, Feb. 25, 2009 (Feb. 25, 2009), 15 pages.
H. Murazaki, "Optimal Setting of Automatic Exposure Control Based on Image Noise and Contrast on Iodine-enhanced CT", Academic Radiology, vol. 19, No. 4, Apr. 1, 2012 (Apr. 1, 2012), 6 pages.
International Search Report PCT/ISA/210 for International Application No. PCT/EP2013/068816 dated Feb. 28, 2014.
Written Opinion of the International Searching Authority PCT/ISA/237 for International Application No. PCT/EP2013/068816 dated Feb. 28, 2014.

* cited by examiner

AUTOMATIC STIPULATION OF A SPECTRAL DISTRIBUTION OF X-RAY RADIATION OF A NUMBER OF X-RAY SOURCES

PRIORITY STATEMENT

This application is the national phase under 35 U.S.C. § 371 of PCT International Application No. PCT/EP2013/068816 which has an International filing date of Sep. 11, 2013, which designated the United States of America, and which claims priority to German patent application number DE 102012217569.5 filed Sep. 27, 2012, the entire contents of each of which are hereby incorporated herein by reference.

FIELD

At least one embodiment of the invention generally relates to a method for automatically stipulating a spectral distribution of x-ray radiation of a number of x-ray sources for multi-energy operation, a method for operating a computed tomography system, a control device for operating a computed tomography system and/or a computed tomography system.

BACKGROUND

Computed tomography systems have been proven in a plurality of applications and are capable of creating desired image information for the respective application. To improve the quality of the image information and to open up new applications projection or imaging information which has been created on the basis of a first spectral distribution of x-ray radiation and a second spectral distribution differing therefrom is frequently used. The terms dual-energy measurement or also multi-energy measurement are used in this context if two or more different spectral distributions are used. A spectral distribution is often abbreviated to "x-ray energy" or "hardness" of the x-ray radiation, since the average energy of the x-ray quanta is indeed produced or changes with the spectral distribution. In such cases the position of the energy maximum of the spectral distribution is generally specified as the value of the x-ray energy. A voltage, mostly in kV, is typically specified as the unit of measure.

A difficulty in such cases is selecting the first and second spectral distributions or energies of the x-ray radiation so that desired image information can be created from the projection information for the respective application. For example the desired image information can be based on a specific medical task or problem. The task can for example include bone structures being removed from the completed CT image (bone removal), of contrast medium information being removed from the completed CT image (virtual non-contrast), of specific crystalline deposits in tissue being recognizable for detecting gout in the completed CT image (gout) or that the extent of a lung embolism can be analyzed (lung dual-energy). In addition it can be necessary—not just in multi-energy operation—to also adapt the spectral distributions used to the examination object, if for example specific anatomical features of the examination object or patient require this.

It is precisely for the adaptation of x-ray energy to the anatomical features of the examination object that the operator of the imaging system needs to have an enormous amount of experience in order to determine the optimum control parameters for creating the desired image information. For example boundary conditions in respect of the radiation dose of the patient are to be taken into account in this process. Therefore a series of methods is known which automates the adaptation of the operating parameters of a computed tomography system or supports it semi-automatically. For multi-energy CT recordings this task is accordingly more difficult.

SUMMARY

At least one embodiment of the invention simplifies the setting of operating parameters of a computed tomography system for multi-energy operation.

At least one embodiment of the invention is directed to a method for automatic stipulation of a spectral distribution of x-ray radiation, a method for operating a computed tomography system, a control device for operating a computed tomography system and/or a computed tomography system.

In accordance with at least one embodiment of the invention, a method for automatic stipulation of a spectral distribution of x-ray radiation of a number of x-ray sources (i.e. at least one, preferably two or more x-ray sources) of a computed tomography system is proposed.

In at least one embodiment of the inventive method, start control parameters of an x-ray source are stipulated which determine the dose and spectral distribution of x-ray radiation of this x-ray source. The start control parameters can in particular be stipulated as a function of the desired image information mentioned at the start, which for example makes a typical dose and a typical spectral distribution necessary. Thus the start control parameters are stipulated which make possible meaningful imaging of an examination object, so that reconstructions of image data for a specific region, such as the heart for example, of the examination object are possible. For example the start control parameters can involve start values of a radiation source voltage and a radiation source current or tube current of the x-ray tube.

At least one embodiment of the invention further relates to a control device for a computed tomography system which has a number of x-ray sources. This control device includes an interface for acquiring the start control parameters of an x-ray source, which define the dose and spectral distribution of x-ray radiation. The interface can for example be connected to the database mentioned or can make possible access to the table likewise mentioned. In addition it is further also conceivable for the interface to acquire inputs of an operator so that the start control parameters can be stipulated interactively.

Furthermore in a development of an embodiment of the method for operating a computed tomography system, based on the expected attenuation of the x-ray radiation by an examination object and expected image information, at least one further system control parameter of the group:

Opening of a detector for x-ray radiation of the computed tomography system,
Rotational velocity about a system axis of the computed tomography system, and
Correction selection parameters for selecting a correction method for the correction of scattered radiation effects of the x-ray radiation, can be stipulated.

Further, especially advantageous embodiments and developments of the invention emerge from the dependent claims as well as the subsequent description, wherein the independent claims of one claim category can also be developed in a similar way to the dependent claims of another claim category.

In at least one embodiment of the inventive method, start control parameters of an x-ray source are stipulated which determine the dose and spectral distribution of x-ray radiation of this x-ray source. The start control parameters can in particular be stipulated as a function of the desired image information mentioned at the start, which for example makes a typical dose and a typical spectral distribution necessary. Thus the start control parameters are stipulated which make possible meaningful imaging of an examination object, so that reconstructions of image data for a specific region, such as the heart for example, of the examination object are possible. For example the start control parameters can involve start values of a radiation source voltage and a radiation source current or tube current of the x-ray tube.

The start control parameters can be stipulated with reference to a standard object which fulfils specific, predetermined anatomical requirements. The start control parameters are thus in this case formed by a type of standard object control parameter in which, during a computed tomography recording of a standard object, an image quality optimal for the respective clinical application is achieved. A standard object can typically be an object which corresponds to a so-called normal patient with the weight of 80 kg. E.g. it is known that for an abdomen examination for a normal patient a tube current of an x-ray tube of 210 mAs at an acceleration voltage of 120 kV is needed. A further example would be a thorax examination with the standard object control parameters: Acceleration voltage 120 kV and tube current 160 mAs. The values are produced from historical experience and are typically predetermined as presetting options in a computed tomography system. In this way suitable presetting options for a patient with the weight of 80 kg are known for very many organs or applications. In addition it is likewise conceivable that during the stipulation of the standard object control parameters, the body size or also the gender of the examination object is taken into consideration. These start control parameters can for example be taken from a known table or database in which control parameters are stored for the standard object involved in order to enable desired image information to be created with the aid of x-ray radiation.

Furthermore in at least one embodiment of the inventive method, proceeding from the start control parameters, an examination-object-specific basic control parameter (examination-object-specific means individual in relation to the examination object from which the x-ray image data is to be prepared) is established, which is based on the expected attenuation of the x-ray radiation by the examination object. The expected attenuation can for example be established automatically from a topogram. A topogram is a fast preliminary recording of the examination object on the basis of which as a rule the subsequent computed tomography imaging is planned. The expected attenuation can however possibly also be established or estimated from other information about the examination object, especially image data from previous examinations. For example a recording with an optical camera could also be employed for estimation, wherein the estimation can be based on a determination of the cross-section or diameter of an examination object.

In such cases particularly the start control parameters known from the database or table are adapted to anatomical circumstances of the individual examination object, in order to ensure that the quality of the image information obtained is not worse compared to a recording made on a standard object. E.g. a start acceleration voltage and a start tube current could be taken from the table mentioned for a recording of the stomach region of the examination object. This start tube current can then for example be further adapted to the examination object in order to stipulate the tube current as an examination-object-specific basic control parameter. Preferably the known method CareDose4D from Siemens can be used for this. It is thus insured that, for the present examination object, which will also be referred to as the patient below, meaningful computed tomography imaging can be created.

Furthermore first target control parameters and second target control parameters for setting the spectral distribution of the x-ray radiation in a subsequent multi-energy measurement of the examination object are stipulated in at least one embodiment of the inventive method. The first and second target control parameters are based in this case likewise on the expected attenuation of the x-ray radiation by the examination object, i.e. they are created as examination-object-specific parameters.

The inventors have recognized here that establishing the target control parameters is especially easily possible if it is already insured that meaningful image information can be created. This is made possible in at least one embodiment of the inventive method by a basic control parameter, which insures the meaningful imaging specific to an examination object being taken into account in the method, i.e. the establishing of the first and second target control parameters on the basis of the examination-object-specific basic control parameter, i.e. for example the examination-object-specific tube current.

If first target control parameters and second target control parameters have been established with at least one embodiment of the inventive method these can be used in an inventive method for operating a computed tomography system.

At least one embodiment of the invention further relates to a control device for a computed tomography system which has a number of x-ray sources. This control device includes an interface for acquiring the start control parameters of an x-ray source, which define the dose and spectral distribution of x-ray radiation. The interface can for example be connected to the database mentioned or can make possible access to the table likewise mentioned. In addition it is further also conceivable for the interface to acquire inputs of an operator so that the start control parameters can be stipulated interactively.

Furthermore, in at least one embodiment, the control device has a dose establishment unit which is embodied, proceeding from the start control parameters, to establish an examination-object-specific basic control parameter. The dose establishment unit takes account in such cases of the expected attenuation of the x-ray radiation by the examination object, which for example can likewise be acquired by the previously mentioned interface.

As an alternative, it is also conceivable for the dose establishment unit or the control unit to have a separate interface for acquiring the attenuation to be expected.

The control device is further equipped with a control parameter establishing unit which is embodied, based on the expected attenuation of the x-ray radiation and the basic control parameter, to automatically establish first target control parameters and second target control parameters for setting a spectral distribution of the x-ray radiation in a subsequent multi-energy measurement on the examination object. The control parameter establishing unit can also be connected to one of the interfaces mentioned for acquiring the expected attenuation of the x-ray radiation or can even have a suitable separate interface.

In addition, at least one embodiment of the invention includes a computed tomography system with a number of x-ray sources and at least one embodiment of the inventive control device.

A majority of the components of the control device, especially the control parameter establishing unit, the dose establishment unit or the interfaces mentioned can be realized entirely or partly in the form of software modules on a processor, preferably of an imaging system. Likewise the control unit, the control parameter establishing unit, the dose establishment unit or the interfaces mentioned can however also be embodied as hardware components, for example in the form of suitably structured ASICs, or as hardware components supported by software. A largely software-based realization has the advantage that even previously used control units can be upgraded in a simple manner by a software update in order to operate in the inventive way. The invention therefore also includes a computer program which is able to be loaded directly into a processor of a programmable computing device, preferably a control device of a computed tomography system, with program code means for executing all steps of the inventive method when the program is executed in the processor.

Further, especially advantageous embodiments and developments of the invention emerge from the dependent claims as well as the subsequent description, wherein the independent claims of one claim category can also be developed in a similar way to the dependent claims of another claim category.

To obtain the target control parameters preferably a number of radiation source voltages (also abbreviated below without restricting their general applicability to x-ray voltage or tube voltage), with which an x-ray source of the imaging system can be operated are each assigned on the basis of a basic control parameter a radiation source current (also abbreviated below without restricting its general applicability to x-ray current or tube current). The different radiation source voltages able to be set in the computed tomography system and available can be predetermined in the form of one or more voltage intervals. They are stipulated for example so that a maximum energy of the x-ray radiation is not exceeded. In such cases the maximum energy of the x-ray radiation can be restricted by a maximum available x-ray voltage. Typically however predetermined, for example legal limit values, are adhered to, so that a permissible radiation load on the patient will not be exceeded.

The x-ray current assigned to a specific x-ray voltage is established respectively in such cases so that it is insured that the x-ray current is sufficiently large, so that during an acquisition of projection data with the selected x-ray voltage, despite the attenuation by the body of the patient (with the given bulk of the patient) a sufficient signal still reaches the detector in order to enable meaningful image information to be reconstructed. In such cases the image quality might fluctuate widely depending on use of the image data or depending on the field of view or clinical application. The optimum image quality depending on the application is if necessary determined by the start control parameters for a standard object. The examination-object-specific basic control parameters are preferably determined so that the image quality which is achieved in a recording with basic control parameters of a patient to be imaged corresponds to the image quality of a recording of the standard object with start control parameters. The image quality in this case is described for example by a specific sharpness or so-called noise. To insure this the basic control parameter (i.e. for example a reference x-ray current adapted to the patient bulk which is calculated for the start x-ray voltage or standard object x-ray voltage) is included in the establishment of the x-ray current assigned to an x-ray voltage. In this way a number of pairs in each case of radiation source voltage and assigned radiation source current are established, which insure on the one hand that meaningful image information is able to be reconstructed for acquired projection data and on the other hand that the hardness of the x-ray radiation does not exceed specific limits.

In an alternate example, the establishing of the pairs can be dispensed with and just a functional description provided, with the aid of which the pairs are able to be established. Thus for example the following formula applies for setting tube current and acceleration voltage so that approximately equally strong image noise is achieved, wherein electronic noise or also the precise spectrum of the x-ray source are ignored: $U^{2,4} \cdot A = CONST$. In this case U is the radiation source voltage and A the radiation source current. With this formula, proceeding from a given current/voltage pair, with the aid of which the value CONST is stipulated, a functional description of any given other pair can be approximately specified. An exact conversion or automatic functional description can for example be achieved with the CareKV product from Siemens, which builds on CareDose4D.

Preferably the radiation source current is assigned to the radiation source voltage on the basis of a water column thickness, wherein the water column thickness is preferably derived or established from the expected attenuation of the x-ray radiation. In this case a thickness of a water column can be established from the topogram using known reference data of water which would cause an attenuation of the x-ray radiation corresponding to the topogram. This means that the expected attenuation of the x-ray radiation by the patient is converted into a water column thickness, so that the attenuation by the patient corresponds to the attenuation by a water phantom with such a water column thickness.

On the basis of the pairs of radiation source voltages and assigned radiation source currents target control parameters can then be established for example.

In an example embodiment of the invention, a pair including radiation source voltage and corresponding radiation source current is established as the first target control parameter, in which the radiation source voltage is minimal and in which at the same time the assigned radiation source current does not exceed a system limit value.

This system limit value is preferably stipulated as follows in this case: Typically in computed tomography systems, for specific radiation source voltages, maximum allowed radiation source currents are predetermined in each case, which insure that a patient is not irradiated with a dose which could lead to damage. In addition the system limit value can also be stipulated so that the computed tomography system and especially the radiation source can be operated reliably. I.e. account can also be taken in the system limit value of the fact that the components of the computed tomography system do not suffer any damage. The maximum radiation source current allowed with regard to the respective radiation source voltage then corresponds for example to the system limit value which is predetermined for the respective radiation source voltage. Thus it can be established, in a similar way to a look-up table, for all established pairs of radiation source voltage and corresponding radiation source currents, whether the radiation source current does not exceed the respective predetermined system limit value.

Thus, of all pairs of x-ray current and x-ray voltage for which the respective system limit value is not exceeded by the x-ray current, precisely the pair is established as first target control parameters which has the lowest x-ray voltage. Thus on the one hand it is insured that the maximum dose which the patient experiences lies within allowable limit values and on the other hand that meaningful image information can be created. In this case a radiation source is activated so that the softest x-ray radiation taking into account the given peripheral conditions (i.e. which has the lowest hardness) is set, which allows a meaningful image information, i.e. which is permissible for an established corresponding radiation source current.

Preferably in addition, a pair including radiation source voltage and corresponding radiation source current is established as second target control parameters in which the corresponding radiation source current does not exceed a system limit value and in which case at the same time the radiation source voltage is at a maximum. The system limit value can in its turn be a radiation source current predetermined by the computed tomography system or external tables. Thus the pair including radiation source voltage and corresponding radiation source current is established as second target control parameters which has the hardest x-ray spectrum with which a radiation source can be activated without a permitted dose being exceeded and for which meaningful image information can be created.

For each radiation source voltage a separate system limit value in relation to the radiation source current can be defined. In this case the pair including radiation source voltage and corresponding radiation source current can be compared in each case with pairs including radiation source voltage and an assigned system limit value. In this case the system limit value can be stipulated as described above for a specific radiation source voltage.

If the first and second target parameters are selected in the previously described way, it is insured that the hardest (most energy-rich) spectrum which creates meaningful image information and also does not damage the patient or also the tomography system, is selected and the softest spectrum which likewise fulfils these peripheral conditions.

Thus the range of meaningfully usable radiation source voltages for the given examination object is exploited to the optimum in order for example, in a subsequent dual-energy measurement, to select a maximum distance between the two x-ray energies. The greater is the energy distance, the more clearly apparent are namely the energy-dependent effects in the images, so that accordingly the image differences are more clearly apparent and the associated information can be better established.

Thus an improvement of the image quality with multi-energy recordings, especially dual-energy recordings, can be achieved by way of embodiments of the invention for numerous applications.

Furthermore in a development of an embodiment of the method for operating a computed tomography system, based on the expected attenuation of the x-ray radiation by an examination object and expected image information, at least one further system control parameter of the group:

Opening of a detector for x-ray radiation of the computed tomography system,
Rotational velocity about a system axis of the computed tomography system, and
Correction selection parameters for selecting a correction method for the correction of scattered radiation effects of the x-ray radiation, can be stipulated.

The opening of the detector in particular involves what is known as a detector collimation, which predetermines the opening angle of the detector used in relation to incident x-ray radiation. The opening of the detector can however also involve the stipulation of a number of detector elements used of an x-ray detector which has a plurality of detector elements. Usually the operator of a computed tomography system namely has the option during recording of selecting between different detector collimations or openings of the detector, in order to exclude negative effects of scattered radiation on the image quality as far as possible. On the one hand the scattered radiation which falls on to an individual detector element increases with the detector collimation. Therefore, with high demands on the image quality there is a tendency for lower collimations or openings of the detector to be recommended.

Furthermore the quality of the images in relation to any movement unsharpness can also depend on the gantry rotation speed and the image quality in its turn can also be restricted by a specific correction method being selected with the aid of the correction selection parameter for correction of scattered radiation effects.

As well as the stipulation of the first and second target control parameters, in a development of the invention the minimization of the scattered radiation effects can additionally be made dependent on expected image information. Expected image information in this case is to be understood within the meaning of the present invention as information regarding the expected image data which is usually created during a recording of a specific examination object or a part of an examination object. The expected image information thus depends on what type of examination object is involved or how the measurement task (the clinical task) is, i.e. whether for example the recording of a chest cavity is involved, the recording of a head or of a specific organ etc. and which type of measurements are to be carried out or which combined images (bone images and/or soft tissue images) are ultimately to be created in a dual-energy method. In this case, for example in the form of a look-up table for the expected image information and the expected attenuation of the x-ray radiation or water column thickness, first and second target control parameters can be established, which are then permanently linked to a specific rotation speed, a specific detector collimation and a specific type of correction method for scattered radiation. Thus an optimum scan mode is produced, i.e. a setting of a preferred complete set of system control parameters for automatic control of an imaging system for specific expected image information when the first and second target control parameters are linked to further system control parameters.

Thus an operator does not need to select these said system control parameters, so that an optimum image quality can be insured for example by using the optimum scan mode for establishing the expected image information.

Embodiments of the invention can be used on different types of computed tomographs.

The method of at least one embodiment can, for example, be used with a computed tomography system which is designed as a single-source system, i.e. only has a single x-ray source. To carry out a dual-energy measurement with the inventive method such a computed tomography system can be controlled so that the x-ray source, during a measurement sequence, i.e. during the acquisition of projection data of an examination object located in a measurement space of the computed tomography system, is operated at times on the basis of the first target control parameters and at times on the basis of the second target control parameters. For example it is conceivable that the x-ray source first performs a half circuit (plus the cone beam angle of the x-ray source) around the measurement space, while it is being operated on the basis of the first target control parameters, in order for example to acquire projection data for a reconstruction of image data with a first x-ray energy, and then performs a further half circuit (plus the fan angle of the x-ray source) while it is being operated on the basis of the second target control parameters, in order to then acquire projection data for example for a reconstruction of image data with a second x-ray energy. As an alternative, during a (multiple) orbit a multiple fast switching between the operation of the x-ray source can also be undertaken between the operation of the x-ray source based on the first target control parameters and the operation of the x-ray source based on the second target control parameters, in order in this way to acquire projection data "almost in parallel" for a reconstruction of image data with the first and the second x-ray energy.

However, the described method is not restricted to computed tomography systems with a single x-ray source. In one development the number of x-ray sources preferably amounts to more than one, for example two, i.e. a dual-source system is involved. A first x-ray source of the computed tomography system can then be operated on the basis of the first target control parameters and a second x-ray source of the computed tomography system on the basis of the second target control parameters. In this case a switch (also a number of times) between the first and the second target control parameters for one or both of the x-ray sources is naturally not excluded, in order in particular to carry out a multi-energy measurement with more than two different x-ray energies.

BRIEF DESCRIPTION OF THE DRAWINGS

The invention is explained once again below with reference to the enclosed figures on the basis of example embodiments. In these example embodiments the same components in different figures are provided with identical reference numbers. In the figures.

DETAILED DESCRIPTION OF THE EXAMPLE EMBODIMENTS

Figure 1:
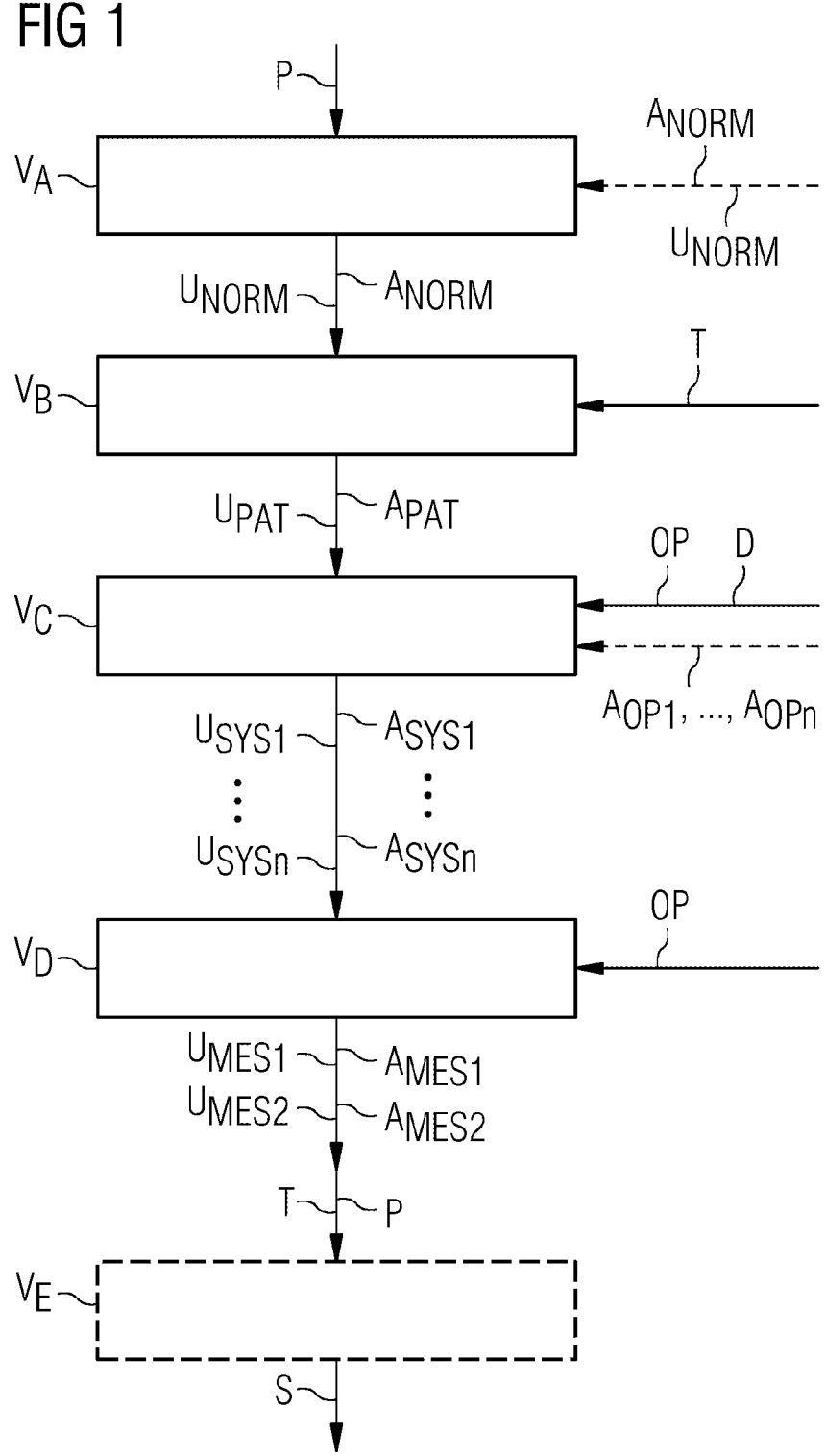
FIG. 1 shows a flow diagram for an example embodiment of a method for stipulation of the spectral distribution of x-ray radiation of a number of x-ray sources.

FIG. 1 shows a method for stipulation of the spectral distribution of x-ray radiation of a number of x-ray sources for dual-energy operation of a computed tomography system. In this figure, in an initial step $V_A$, start control parameters $A_{NORM}$, $U_{NORM}$ of the x-ray sources are stipulated on the basis of expected image information, i.e. based on information about the type of examination object or of the clinical task. The start control parameters involve start values for control parameters which determine the dose of the emitted x-ray radiation in the spectrum of the emitted x-ray radiation.

With an x-ray tube, the spectrum is determined as a rule by an acceleration voltage (x-ray voltage) between an electron source and a target. The dose is given by a function of the x-ray voltage and a tube current of the x-ray tube. The two-tuple of start x-ray voltage $U_{NORM}$ and start tube current $A_{NORM}$ thus forms the start control parameters $A_{NORM}$, $U_{NORM}$.

These start control parameters $A_{NORM}$, $U_{NORM}$ are as a rule known for a standard object or for a standard patient and can for example be taken directly from a look-up table or database if the type of examination object and/or the clinical task is known. Therefore it can be sufficient, instead of the start control parameters, to optionally predetermine expected image information P from which the start control parameters $A_{NORM}$, $U_{NORM}$ or standard control parameters can be determined with the aid of the table.

For example for a standard patient who has a weight of 80 kg, for an abdomen examination, x-ray voltage $U_{NORM}$ of 120 kV and a tube current of 120 mAS can be taken from the table. These standard control parameters ensure that sufficient projection data can be created for a standard patient in order to create the expected image information P. This means that in this case a recording of the stomach region can be undertaken the aid of a computed tomography system which is operated with the standard control parameters $A_{NORM}$, $U_{NORM}$ if the patient corresponds to a standard patient.

As a rule however the patient intended for examination differs anatomically from the standard patient, so that it is inevitable to stipulate or to establish examination-object-specific basic control parameters $U_{PAT}$, $A_{PAT}$ which make possible computed tomography imaging of the patient with the expected image information P. This is done as part of a further method step $V_B$. The examination-object-specific basic control parameters $U_{PAT}$, $A_{PAT}$, i.e. the patient-individual parameters tube current $A_{PAT}$ and tube voltage $U_{PAT}$, are established on the basis of the standard control parameters $A_{NORM}$, $U_{NORM}$.

In addition topogram data T is taken into consideration and included for the planning of the subsequent x-ray examination. The topogram data T reflects an expected attenuation of the x-ray radiation by the examination object or the patient. From the topogram T for example a water column thickness D can be established which corresponds to the thickness of a water phantom in the unit cm, which causes the same attenuation of x-ray radiation as the patient.

From the three-tuple, including the start control parameters $A_{NORM}$, $U_{NORM}$ and the water column thickness D, examination-object-specific basic control parameters $U_{PAT}$, $A_{PAT}$ can then be calculated for example with a known method such as the known CareDose4D method, which parameters predetermine a patient-individual tube voltage $U_{PAT}$ and a patient-individual tube current $A_{PAT}$. This means that the basic control parameters $U_{PAT}$, $A_{PAT}$ now stipulate a dose in relation to the x-ray radiation and a spectrum of the x-ray radiation used which make it possible, for the patient to be examined, to create the expected image information P with the aid of the computed tomography system. The examination-object-specific basic control parameters $U_{PAT}$, $A_{PAT}$ initially relate to the operation of the computed tomography system with a single acceleration voltage for an x-ray tube. This mode of operation is also known as single-energy operation.

The present inventive computed tomography system has the option of multi-energy operation however. This means that an x-ray tube is operated at a least part of the time with a first acceleration voltage $U_{MES1}$ and a second acceleration voltage $U_{MES2}$ during a measurement sequence. Thus, as stated at the start, additional options exist for obtaining expected image information P. With the aid of the steps $V_C$ and $V_D$ described below, optimum target control parameters $U_{MES1}$, $A_{MES2}$ and $U_{MES2}$, $A_{MES2}$, i.e. tube currents $A_{MES1}$, $A_{MES2}$ and tube voltages $U_{MES1}$, $U_{MES2}$, will now be established for dual-energy operation.

For this purpose, in step $V_C$, account is initially taken of configuration data OP of the computed tomography system. Typically the configuration data OP contains a specification about the tube voltages $U_{SYS1}, \ldots U_{SYSn}$ with which an x-ray tube of the computed tomography system can be operated. This data is available for example through a database or through the computed tomography system itself.

For the tube voltages $U_{SYS1}, \ldots, U_{SYSn}$ predetermined in the configuration data OP—or optionally in a specific grid with a predetermined spacing between voltages $U_{SYS1}, \ldots, U_{SYSn}$—a suitable tube current $U_{SYS1}, \ldots, U_{SYSn}$ is further determined in each case. This can be made available for example in the form of a look-up table for subsequent steps.

To calculate the appropriate tube voltages $A_{SYS1}, \ldots, A_{SYSn}$ in each case, once again the water column thickness D, which has been established based on the topogram data T, is to be taken into account. For example the tube current $U_{SYS1}$ for the tube voltage $U_{SYS1}$ can, by way of example, be calculated as follows:

$$A_{SYS1} = \frac{U_{PAT}^{2,3} \cdot A_{PAT} \cdot e^{\mu_{SYS1} \cdot D}}{U_{SYS1} \cdot e^{\mu_{SYS1} \cdot D}} \quad (1)$$

In this equation $\mu_{SYS1}$ and $\mu_{PAT}$ are attenuation coefficients which express how strongly the x-ray radiation is attenuated with a given spectrum or given energy or tube voltage $U_{SYS1}$ or $U_{PAT}$ by an object per centimeter of water thickness D. This means the attenuation coefficients $\mu_{SYS1}$, $\mu_{PAT}$ are standardized to a water phantom and are likewise able to be taken from a table or database. It is also possible to carry out a prior calibration measurement for determining the respective attenuation coefficients $\mu_{SYS1}$, $\mu_{PAT}$. Thus, with the aid of the equation (1), for each possible setting of the computed tomography system relating to the tube voltage $U_{SYS1}, \ldots, U_{SYSn}$ an associated tube current $A_{SYS1}, \ldots, A_{SYSn}$ will be established, which makes it possible for the expected image information P to be created.

The tube currents $A_{SYS1}, \ldots, A_{SYSn}$ assigned in this case to the tube voltage $U_{SYS1}, \ldots, U_{SYSn}$ do not initially yet take into account however that specific dose values are to be adhered to in order not to endanger or to damage the patient. Typically these limits are however already present as system limit values $A_{OP1}, \ldots, A_{OPn}$, mostly in the configuration data OP of the computed tomography system. As an alternative they can also be predetermined in another way, for example by a database, an available table or an operator entry, as is shown by the dashed line. In order not to exceed a specific dose, a maximum tube voltage $A_{OP1}, \ldots A_{OPn}$ is present for example for each of the possible tube voltages of the computed tomography system for which the limit values for protecting the patient are safely adhered to.

In step $V_D$ a minimum tube voltage $U_{MES1}$ can now be defined, of which the assigned tube current $A_{MES2}$ does not exceed the maximum tube current $A_{OP1}, \ldots, A_{OPn}$ for the respective acceleration voltage $U_{MES1}$ predetermined for example by the configuration data $O_P$ of the imaging system. The tuple from the minimum tube voltage $U_{MES1}$ and the associated allowable tube current $A_{MES1}$ (i.e. lying below the respective system limit value $A_{OP1}, \ldots, A_{OPn}$) in this case forms the sought-after first target control parameters $U_{MES1}, \ldots, A_{MES1}$. Further in step D second target control parameters $U_{MES2}$, $U_{MES2}$ are determined so that the second tube voltage $U_{MES2}$ is at its maximum, but the associated tube current $A_{MES2}$ does not exceed the system limit value $A_{OP1}, \ldots, A_{OPn}$ of the tube current given by the configuration data $O_P$ in relation to the tube voltage $U_{MES2}$.

Thus, at the end of step VD first target control parameters $U_{MES1}$, $A_{MES1}$ and second target control parameters $U_{MES2}$, $U_{MES2}$ are stipulated, which have the maximum possible x-ray energy difference for the respective clinical task and the current examination object, for which it is insured that, both with first and also with the second target control parameters, expected image information P can be created in this way. If for example the first target control parameters $U_{MES1}$, $A_{MES1}$ are used for setting the x-ray source for the acquisition of the projection data for the high-energy image data and the second target control parameters $U_{MES2}$, $U_{MES2}$ are used for setting the x-ray source for the acquisition of the projection data for the low-energy image data, then it is ultimately guaranteed that a sufficiently good low-energy image and a high-energy image of the examination object with (under the given actual conditions) maximum possible energy difference are available for further processing. The terms "low-energy image" and "high-energy image" are to be understood relative to one another in this case, i.e. the high-energy image is created with harder x-ray radiation than the low-energy image.

As well as this optimization achieved by the maximum possible spacing between the x-ray energies, yet further measures can also contribute to improving the quality of the created image data.

For operating the computed tomography system further system control parameters S are used, such as for example the opening of an x-ray detector, the speed of rotation of the gantry or the option for setting different correction methods for minimizing scattered radiation effects. In order for example to establish an optimum scan mode, these further control parameters S can likewise be adapted on the basis of the examination object. This is done in an optional step $V_E$, which for example can also be executed when the water column thickness D or the topogram T or the expected image information P are known. This means that the optional step $V_E$ could also already be executed after the step $V_B$ or $V_C$.

For example the following look-up table could be used to predetermine the further control parameters.

| Water column thickness | Expected image information | Scan mode |
|---|---|---|
| <30 cm | Bone removal | Mode 1 |
| 30 cm | Bone removal | Mode 2 |
| <30 cm | Liver VNC | Mode 2 |
| >30 cm | Liver VNC | Mode 2 |

The scan mode, i.e. mode 1 or mode 2, predetermines in this case the control parameters detector collimation (Det. coll.), rotation velocity of the gantry (Rot. velocity) and correction selection parameters (Cor. sel.) for example in accordance with the following table:

| Scan mode | Det. coll. | Rot. velocity | Cor. Sel. |
|---|---|---|---|
| Mode 1 | 64 × 0.6 mm | 0.5 sec/rev | Type 1 |
| Mode 2 | 32 × 0.6 mm | 0.5 sec/rev | Type 2 |

This information is to be interpreted as follows here.

Based on a specific water column thickness D of the patient, for example if the patient is assigned a water column thickness D of less than 30 cm, and based on the expected image information P, which include for example of specific bone configurations being calculated out of the completed computed tomography image (bone removal), a scan mode can be set with further control parameters S, for example in accordance with mode 1. I.e. the further control parameters S include a rotation velocity of the gantry $V_{ROT}$, which in accordance with the above table in mode one 1 amounts to 0.5 sec/rev. In addition the further control parameters S contain a detector collimation for which, for example in accordance with mode 1 in the above table, projection information can be acquired simultaneously from a slice of the examination object with the aid of an x-ray detector with 64 detector elements, wherein related to the completed image data, i.e. calculated back to the isocenter, the slice thickness amounts to 0.6 mm. In addition the further control parameters S include a correction selection parameter CM, with which the manner in which the correction of scattered radiation effects can be undertaken can be stipulated. In accordance with the above table a type 1 has been stipulated as correction selection parameter in accordance with mode 1 for the correction of the scattered radiation. For a type 1 scattered radiation effect correction for example 40 extra sensors are used, which are for example not suitable for detection of an imaging projection measurement signal. These extra sensors only serve to acquire scattered radiation information, on the basis of which scattered radiation effects can be computed out of the image data.

The further entries in the above tables are to be interpreted in a similar way. In these tables the expected image information "liver-VNC" means that with a liver tomogram information relating to a contrast medium saturation of the liver is to be computed out of the image data. Furthermore the correction selection parameter "Type 2" means that for example 32 detector elements present in any event on an x-ray detector which are not disposed in the direct projection area of the x-ray radiation are used to acquire scattered radiation information, on the basis of which the scattered radiation effects can be computed out of the tomogram.

The further control parameters S are above all suited to optimizing the influence of scattered radiation on the image quality which is changed by geometry and attenuation characteristics of the irradiated object. In this case account is taken in particular of the fact that for different expected image information different acceleration voltages are also used, which then in their turn result in different scattered radiation. The combination of the stipulation of the optimized parameter set of target control parameters $A_{MES1}$, $A_{MES2}$, $U_{MES1}$, $U_{MES2}$ and further control parameters S for stipulation of a fully automatic scan of an examination object thus makes possible both an optimum setting of the x-ray sources of the computed tomography system in respect of multi-energy operation and simultaneously, based on the settings, the reduction or correction of scattered radiation effects by predetermining further control parameters S. The optimum settings for the further control parameters S can for example be based on previously performed calibration measurements and thus be made available in the form of a look-up table as described above for other expected image information P as well, such as for example the "gout" or "lung dual-energy" measurements described above.

Thus the method based on topogram data T or on the extracted attenuation information automatically offers an optimum combination for a multi-energy recording from first target control parameters and second target control parameters as well as corresponding collimations.

Figure 2:
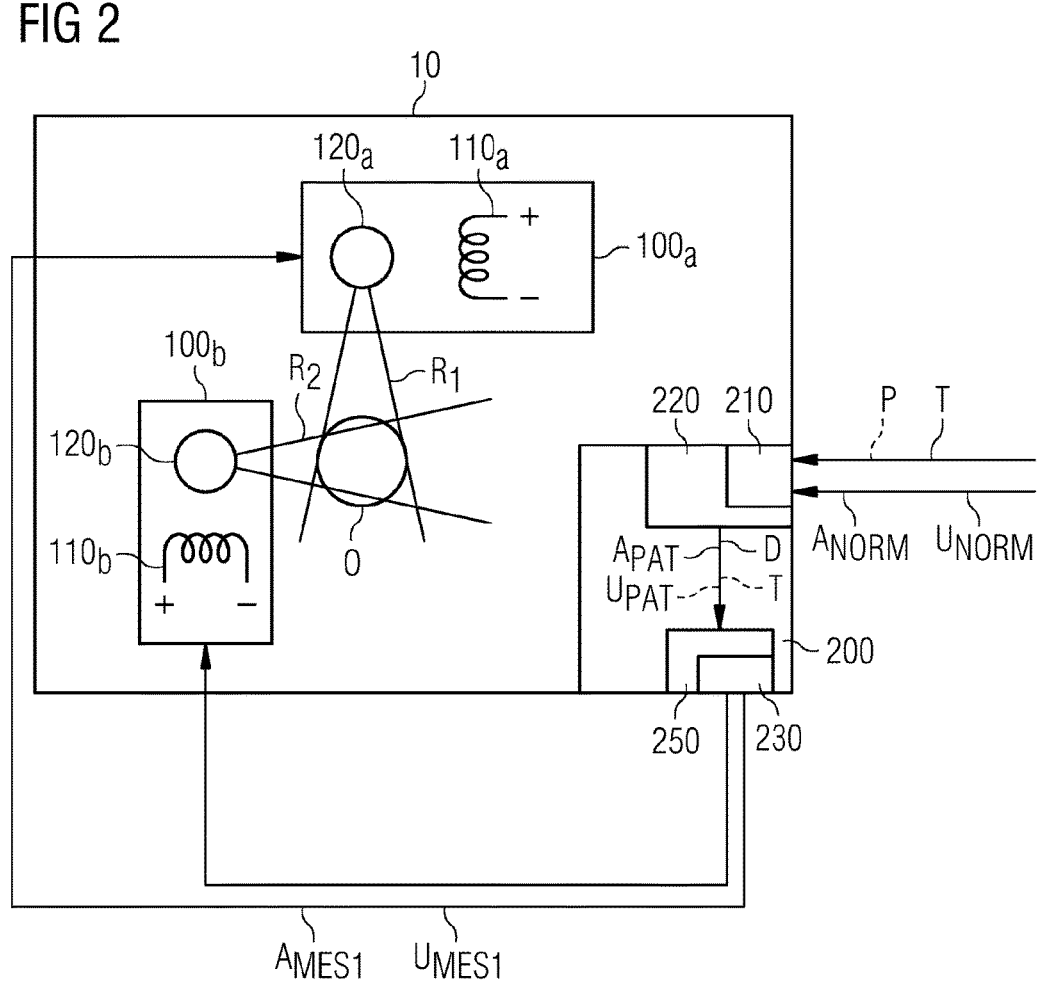
FIG. 2 shows a schematic diagram of an example embodiment of a computed tomography system which is embodied for automatic stipulation of the spectrum of a number of x-ray sources.

FIG. 2 shows a rough schematic diagram of the structure of an inventive computed tomography system 10.

The CT-System 10 essentially includes in this case of a normal scanner in which on a gantry a projection measurement data acquisition system with a detector (not shown) and an x-ray source $100_a$, $100_b$ lying opposite the detector circulates around a measurement chamber. In the example shown the CT system is a dual-source computed tomography system 10 with two x-ray sources $100_a$, $100_b$ disposed on the gantry at 90° to one another and a detector lying opposite said sources in each case. In front of the scanner is located a patient table (likewise not shown), the upper part of which can be moved with a patient O located thereon relative to the scanner in order to be able to move the patient O relative to the projection measurement data acquisition system through the measurement space.

The scanner and the patient table are activated by a tomograph control device 200, from which control data can be sent via a usual control interface 230 in order to control the tomograph in accordance with one or more predetermined protocols in a known manner. The control data includes inter alia the target control parameters $A_{MES1}$, $U_{MES1}$, $A_{MES2}$ $U_{MES2}$ for the x-ray sources 100a, 100b. In this case the x-ray source 100a has an electron source 110a which emits electrons onto a target 120a. The x-ray source 100a is operated in this case with a tube current $A_{MES1}$ and an acceleration voltage $U_{MES2}$ and emits x-ray radiation $R_1$ in the direction of an examination object O. The x-ray radiation $R_1$ irradiates the examination object O, so that projection data is obtained therefrom which reproduces an attenuation of the x-ray radiation $R_1$ by the examination object O. Likewise the second x-ray source 100b has an electron source 110b which is operated with the tube current $A_{MES2}$ and sends out electrons in the direction of the target 120b which have been accelerated with an acceleration voltage $U_{MES2}$. In this case an x-ray radiation $R_2$ is created which is sent out in the direction of the examination object O and likewise irradiates said object so that projection data can also be created on the basis of the radiation of the x-ray radiation $R_2$.

Through the movement of the patient O along the system axis, and the simultaneous circulation of the radiation sources a three-dimensional spatial area of the patient O can be acquired in such cases. In particular the x-ray sources $100_a$, $100_b$ can describe a helical trajectory during the measurement related to a coordinate system defined as a fixed coordinate system in relation to the patient O. The detectors in this case acquire projection measurement data which is transferred to a measurement data interface of the control device 200 not shown in the diagram for reasons of clarity. This projection measurement data is then further processed in a reconstruction device.

The x-ray radiations $R_1$ and $R_2$ can differ in such cases in respect of their spectrum, i.e. their energy and their intensity, so that with the two projection measurement data acquisition systems the projection measurement data for the reconstruction of high-energy image data and for the reconstruction of low-energy image data of a dual-energy measurement can be created simultaneously.

The finished reconstructed computed tomography image data (volume image data and/or slice images) is then transferred to an output interface which then stores the image data for example in a memory of the control device 200 and/or transfers it for output on a screen of a user interface of the control device 200. Furthermore the image data can be fed via the output interface into a network connection connected to computed tomography system, for example a Radiological Information System (RIS) or another medical image processing system, such as PACS for example, or stored in mass storage present in such systems, or printed out at printers on such systems. The data can also be further processed in any given way and then if necessary stored or output.

In order to now be able to operate the computed tomography system 10 with the inventive method explained above in the optimum way, the control device 200 and also has the following components:

In a dose establishing unit 220, on the basis of the water column thickness D and the start control parameters $A_{NORM}$, $U_{NORM}$, the patient-individual basic control parameters $A_{PAT}$ or $U_{PAT}$ are established. This data D, $A_{NORM}$, $U_{NORM}$ is received by the dose establishing unit 220 as well as the expected image information P, i.e. information about the examination object type and the clinical tasks, and possibly topogram data T which contains patient-individual or examination-object-specific attenuation information, via an interface 210 of the computed tomography system 10.

As mentioned, the dose establishing unit 220 can operate for example on the basis of the known CareDose4D algorithm. In the example shown in FIG. 2 the basic control parameter $U_{PAT}$ corresponds as regards the tube voltage to the standard control parameter $U_{NORM}$. The basic control parameter $A_{PAT}$, which corresponds to a patient-individual tube current $A_{PAT}$, is transferred to a control parameter establishing unit 250, which as described above, establishes a first pair or two-tuple of target control parameters $U_{MES1}$, $A_{MES1}$ and transfers these with the aid of a control interface 230 each case to the first x-ray source 100a and establishes a second pair or two-tuple of target control parameters $U_{MES2}$, $U_{MES2}$ and transfers these to a second x-ray source 100b. Thus the one x-ray source 100a, will be operated with a high energy, stipulated by the voltage value $U_{MES1}$ of the first target control parameters $U_{MES1}$, $A_{MES2}$, and the other x-ray source 100b will be operated with a lower energy by comparison, stipulated by the voltage value $U_{MES2}$ of the second target control parameters $U_{MES2}$, $U_{MES2}$. In this case it should be pointed out that the control device 200 shown schematically as one block can also be constructed from a number of functionally-linked components, which can be disposed spaced at a distance from one another. For example the dose establishing unit 220, the control parameter establishing unit 250 and also the interface 210 can be embodied separately in relation to the other components of the control device 200, for example as a self-contained module or in the form of software on a separately programmable computing device.

Figure 3:
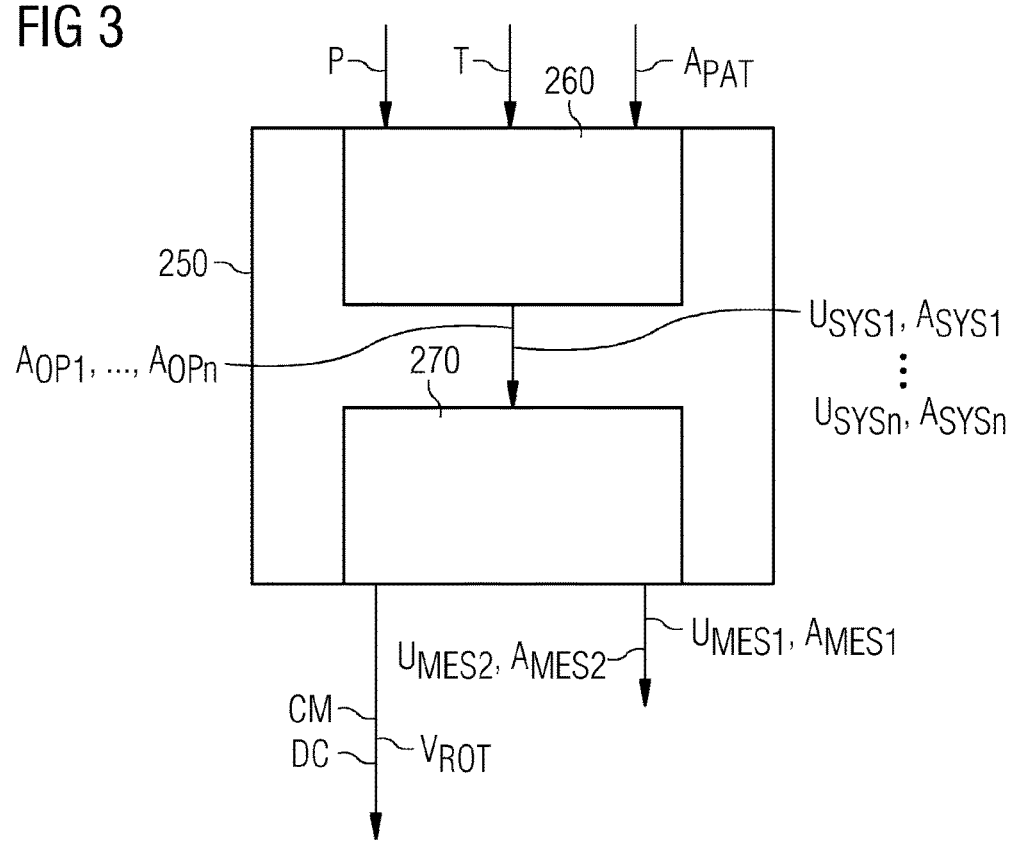
FIG. 3 shows a schematic detailed view of a control parameter establishing unit which automatically establishes target control parameters for operation of a number of x-ray sources.

How the maximum difference between the x-ray energies can be achieved is illustrated once again more precisely in FIG. 3. To this end the control parameter establishing unit 250 has an optimization unit 260, which on the basis of the patient-individual tube current $A_{PAT}$ and the patient-individual attenuation information, i.e. the topogram data T or a water column thickness D, performs the optimization. As already described in relation to FIG. 1, two-tuples are computed in each case, including possible acceleration voltages $U_{SYS1}, \ldots, U_{SYSn}$ with corresponding tube current $A_{SYS1}$ to $A_{SYSn}$, so that the expected image information P can be created with the aid of the calculated tuples $A_{SYS1}$, $U_{SYS1}$ to $A_{SYSn}$, $U_{SYSn}$. This data is transferred to a correlation unit 270 which performs the comparison with configuration data OP of the imaging system, i.e. a comparison with system limit values $A_{OP1}$, $A_{OPn}$ of the tube current, which are predetermined by the imaging system for acceleration voltages, wherein then first target control parameters $U_{MES1}$, $A_{MES1}$ and second target control parameters $U_{MES2}$, $A_{MES2}$, as described in relation to FIG. 1, are established.

In addition the expected image information P can also be transferred to the optimization unit 260. On the basis of the expected image information P, further control parameters can then be established by the optimization unit 260 as likewise described in relation to FIG. 1, for each tuple $U_{SYS1}$, $A_{SYS1}$, for example the detector opening DC, the gantry rotation velocity $V_{ROT}$ and a correction selection parameter CM, which makes it possible to switch between different methods for scattered radiation correction. The parameters thus established are then preferably transferred to the control interface 230 shown in FIG. 2 so that the control interface 230 can make available all parameters which describe a scan mode. This means that no additional interventions by the operator are necessary in order to determine an optimum scan mode.

Finally it should be pointed out that the features of all the example embodiments or further developments disclosed in figures can be used in any given combination. It is likewise finally also pointed out that the method, the control device or the computed tomography system described above in detail merely involve example embodiments which can be modified by the person skilled in the art in a wide diversity of ways without departing from the field of the invention. The method is for example, as already explained, also able to be used on computed tomography systems with only one x-ray source. Likewise the computed tomography system can however also, in addition to the two x-ray sources shown in FIG. 1, have x-ray sources with which it can then be insured with the inventive method that the energy spacings between the energies of the different x-ray sources are optimized. Furthermore the use of the indefinite article "a" or "an" does not exclude the features concerned also being present multiple times. Likewise the terms "unit" or module do not exclude the components concerned including a number of interacting subcomponents, which if necessary can also be spatially distributed.

The invention claimed is:

1. A method for establishing parameters for setting a spectral distribution of x-ray radiation of at least two x-ray sources of a computed tomography system, the method comprising:
    stipulating start control parameters of an x-ray source, the start control parameters being useable to determine a dose and a spectral distribution of x-ray radiation;
    establishing an examination-object-specific basic control parameter, based on an expected attenuation of the x-ray radiation by an examination object and proceeding from the start control parameters;
    establishing, based on the expected attenuation of the x-ray radiation by the examination object and the basic control parameter, first target control parameters of a first x-ray source and second target control parameters of a second x-ray source for setting the spectral distribution of the x-ray radiation in a subsequent multi-energy measurement on the examination object;
    setting first and second radiation tube source voltages based on the first and second target control parameters in the subsequent multi-energy measurement; and
    setting a first spectral distribution of x-rays and second spectral distribution of x-rays based on the first and second target control parameters in the subsequent multi-energy measurement.

2. The method of claim 1, wherein a number of radiation source voltages, with which an x-ray source of the computed tomography system is operable, are each assigned a radiation source current on the basis of the basic control parameter.

3. The method of claim 2, wherein the radiation source current is assigned to the radiation source voltage on the basis of a water column thickness.

4. The method of claim 3, wherein the water column thickness is established from the expected attenuation of the x-ray radiation.

5. The method of claim 2, wherein a pair including radiation source voltage and assigned radiation source current is established as first target control parameters, in which the radiation source voltage is minimal and at the same time the assigned radiation source current does not exceed a first system limit value.

6. The method of claim 1, wherein a pair including radiation source voltage and assigned radiation source current is established as first target control parameters, in which the radiation source voltage is minimal and at the same time the assigned radiation source current does not exceed a first system limit value.

7. The method of claim 1, wherein a pair including radiation source voltage and assigned radiation source current is established as second target control parameters, in which the radiation source voltage is maximal and at the same time, the assigned radiation source current does not exceed a second system limit value.

8. A method for operating a computed tomography system, comprising:
establishing first target control parameters and second target control parameters with the method of claim 1; and
operating a number of x-ray sources of the computed tomography system on the basis of the established first target control parameters and the second target control parameters.

9. The method of claim 8, wherein, based on the expected attenuation of the x-ray radiation by an examination object and an expected image information, at least one of the further system control parameters of the group is stipulated to
open a detector for x-ray radiation of the computed tomography system,
be a gantry rotational velocity, or correct selection parameters for selecting a correction method for the correction of scattered radiation effects of the x-ray radiation is stipulated.

10. The method of claim 9, wherein an x-ray source is operated during a measurement sequence for part of the time on the basis of the first target control parameters and for part of the time on the basis of the second target control parameters.

11. The method of claim 8, wherein an x-ray source is operated during a measurement sequence for part of the time on the basis of the first target control parameters and for part of the time on the basis of the second target control parameters.

12. The method of claim 8, wherein the number of the x-ray sources amounts to more than one.

13. The method of claim 12, wherein a first x-ray source of the x-ray sources of the computed tomography system is operated on the basis of the first target control parameters and a second x-ray source of the x-ray sources of the computed tomography system is operated on the basis of the second target control parameters.

14. The method of claim 1, wherein the number of the x-ray sources amounts to more than one.

15. The method of claim 14, wherein a first x-ray source of the x-ray sources of the computed tomography system is operated on the basis of the first target control parameters and a second x-ray source of the x-ray sources of the computed tomography system is operated on the basis of the second target control parameters.

16. A non-transitory computer program product, directly loadable into a processor of a programmable processing device, including program code segments to the method of claim 1 when the program is executed in the processor.

17. The method of claim 1, further comprising setting a maximum distance between a first x-ray energy and a second x-ray energy based on the first and second target control parameters in the subsequent multi-energy measurement.

18. A control device for a computed tomography system including a number of x-ray sources, the control device comprising:
a first interface, to acquire the start control parameters of an x-ray source of the computed tomography system, useable to determine a dose and spectral distribution of x-ray radiation;
a second interface, to acquire an expected attenuation of the x-ray radiation by an examination object to be examined; wherein the control device is
configured, based on the expected attenuation of the x-ray radiation proceeding from the start control parameters, to establish an examination-object-specific basic control parameter; and
configured, based on the expected attenuation of the x-ray radiation and the basic control parameter, to automatically establish first target control parameters and second target control parameters, useable to set a spectral distribution of the x-ray radiation in a subsequent multi-energy measurement on the examination object;
configured to set first and second radiation tube source voltages based on the first and second target control parameters in the subsequent multi-energy measurement; and
configured to set a first spectral distribution of x-rays and second spectral distribution of x-rays based on the first and second target control parameters in the subsequent multi-energy measurement.

19. A computed tomography system comprising:
the number of x-ray sources; and
the control device of claim 18.

20. The control device of claim 18, wherein the control device is further configured to operate a first x-ray source at a first voltage and to simultaneously operate a second x-ray source at a second voltage different from the first voltage.

* * * * *